United States Patent [19]
Makino et al.

[11] Patent Number: 5,534,534
[45] Date of Patent: Jul. 9, 1996

[54] PHARMACEUTICAL COMPOSITIONS FOR ORAL USE AND METHOD OF PREPARING THEM

[75] Inventors: Tadashi Makino; Yashio Mizukami; Jun-ichi Kikuta, all of Osaka, Japan

[73] Assignee: Takeda Chemical Industries, Ltd., Osaka, Japan

[21] Appl. No.: 978,290

[22] Filed: Nov. 18, 1992

[30] Foreign Application Priority Data

Nov. 20, 1991 [JP] Japan .................................. 3-304924

[51] Int. Cl.$^6$ .................................................. A61K 31/415
[52] U.S. Cl. ...................... 514/388; 514/381; 514/772.3; 514/772.4
[58] Field of Search .................................. 514/381, 388, 514/772.3, 772.4

[56] References Cited

U.S. PATENT DOCUMENTS

| | | | |
|---|---|---|---|
| 4,880,804 | 11/1989 | Carini et al. | 514/253 |
| 5,128,356 | 7/1992 | Naka | 514/381 |

FOREIGN PATENT DOCUMENTS

| | | |
|---|---|---|
| 230298 | 7/1987 | European Pat. Off. . |
| 280999 | 9/1988 | European Pat. Off. . |
| 347767 | 12/1989 | European Pat. Off. . |
| 344795 | 12/1989 | European Pat. Off. . |
| 392317 | 10/1990 | European Pat. Off. . |
| 399732 | 11/1990 | European Pat. Off. . |
| 400835 | 12/1990 | European Pat. Off. . |
| 420237 | 4/1991 | European Pat. Off. . |
| 425921 | 5/1991 | European Pat. Off. . |
| 426021 | 5/1991 | European Pat. Off. . |
| 459136 | 12/1991 | European Pat. Off. . |
| 2251199 | 5/1974 | Germany . |
| WO9116313 | 10/1991 | WIPO . |

OTHER PUBLICATIONS

Seta et al., "Preparation and pharmacological evaluation of captopril sustained–release dosage forms using oily semi-solid matrix", *International Journal of Pharmaceuticals*, vol. 413 1988, pp. 255–262.

JP–B–57–45206/1982.

*Remington's Pharmaceutical Sciences*, 17th Edition Alfonso Gennaro Ed., pp. 1305; 1306, 1478–1480; 653–666 (1985).

*Handbook of Pharmaceutical Excipients*, American Pharmaceutical Assoc. 1986, ISBN (U.S.) 0–917 330–56–0. p. 213.

Primary Examiner—Marianne M. Cintins
Assistant Examiner—Keith MacMillan
Attorney, Agent, or Firm—Foley & Lardner

[57] ABSTRACT

A pharmaceutical composition for oral use comprising an effective amount of a compound of the formula (I) having antagonistic action to angiotensin II

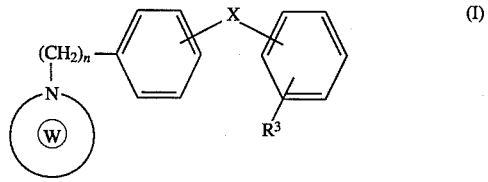

(wherein the ring W is an optionally substituted N-containing heterocyclic residue; $R^3$ is a group capable of forming an anion or a group convertible thereinto; X is a direct bond or a spacer having an atomic length of two or less between the phenylene group and the phenyl group; and n is an integer of 1 or 2) and an oily substance having a lower melting point, and a method for preparing a pharmaceutical composition for oral use comprising an effective amount of a compound of the formula (I) and an oily substance having a lower melting point, which comprises admixing the compound of the formula (I) with an oily substance having a lower melting point and then subjecting the mixture to molding.

27 Claims, No Drawings

PHARMACEUTICAL COMPOSITIONS FOR ORAL USE AND METHOD OF PREPARING THEM

FIELD OF THE INVENTION

This invention relates to orally administrable pharmaceutical compositions capable of suppressing decomposition of the active component contained therein and maintaining excellent stability over time and method of preparing them.

More specifically, the present invention relates to a pharmaceutical composition for oral use comprising an effective amount of a compound of the formula (I) having antagonistic action to angiotensin II

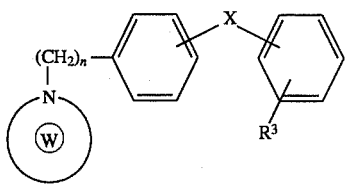

, wherein the ring W is an optionally substituted N-containing heterocyclic residue; $R^3$ is a group capable of forming an anjou or a group convertible thereinto; X is a direct bond or a spacer having an atomic length of two or less between the phenylene group and the phenyl group; and n is an integer of 1 or 2, and an oily substance having a lower melting point, which is effective for the therapy of, among others, hypertension and congestive heart failure, and to a method of preparing the composition.

BACKGROUND OF THE INVENTION

In the field of therapy of hypertension, angiotensin II (AII) receptor antagonist (AIIA) has attracted attention as an effective agent for the therapy of hypertension following angiotensin I converting enzyme (ACE) inhibitors. A compound of the formula (I), for example, benzimidazole-7-carboxylic acid and derivatives thereof having a strong anti-AII action (cf. EP Publication No.-0425921 A1 official gazette and EP Publication No. 0459136 A1 official gazette) are considered to have, for example, the following advantages as compared with ACE inhibitors.

1) It has been known that there are a series capable of producing AII, which are not in the series of ACE. For example, benzimidazole-7-carboxylic acid and derivatives thereof also inhibit the action of this AII which is not dependent on ACE, and therefore it may well be that these compounds exhibit a stronger and more effective hypotensive action than that of ACE inhibitors.

2) Since benzimidazole-7-carboxylic acid and derivatives thereof do not enhance the action of bradykinin observed in ACE inhibitors, they are less likely to cause coughing as a side effect.

OBJECT OF THE INVENTION

However, while the compounds of the formula (I) having antagonistic action to angiotensin II, for example, benzimidazole-7-carboxylic acid and derivatives thereof, useful as therapeutic agent of hypertension are stable against temperature, moisture and light when they are alone in the solid state, when they are prepared into tablets of a formulation incorporated with other ingredients, it has been observed that lowering of the content of the active ingredient is apt to be enhanced with the lapse of time due to deformation of crystals caused by, for example, pressure, abrasion and heat, applied in the step of granulation or molding under elevated pressure in the course of preparation.

While research and development of the compound of the formula (I) (hereinafter sometimes called "active component") thereof as therapeutic agent of hypertension have been conducted, problems with respect to the stability in the course of preparation are not satisfactorily solved yet. Especially, no practical technique for improving the stability of a benzimidazole-7-carboxylic acid and derivatives thereof contained in the preparation, by sufficiently suppressing decomposition of the active component with the lapse of time, the decomposition being observed in the case where the active component is formulated into a solid preparation such as tablets, has been established yet. Thus, the object of this invention is to provide stabilized preparations of the compound of the formula (I) having antagonistic action to angiotensin II. Furthermore, the present invention aims at a sufficiently practical method of stabilization from the economical viewpoint as well, without resorting to a method inevitably requiring increased cost, such as that involving use of an excess amount of the active component or extremely minimizing the moisture content. The present invention is also to heighten the value of finished products by prolonging the period expiration through improved stability of the compositions.

In view of the circumstances described as above, the present inventors attempted various means of general use in order to realize the stabilization of compositions containing the compound of the formula (I) having antagonistic action to angiotensin II. In no compositions prepared thus above, however, was found a satisfactorily practical stabilizing effect. The present inventors further continued various investigations, and unexpectedly found that, by incorporating an oily substance having a low melting point into a formulation containing the compound of the formula (I) having antagonistic actions to angiotensin II, decomposition of the active component is remarkably suppressed to afford a stable composition, and further investigations were conducted repeatedly to accomplish the present invention.

SUMMARY OF THE INVENTION

An object of the present invention is to provide
(1) a pharmaceutical composition for oral use comprising an effective amount of a compound of the formula (I) having antagonistic action to angiotensin II

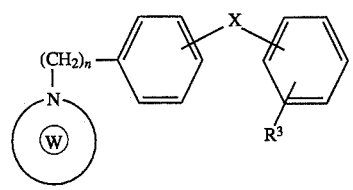

(wherein the ring W is an optionally substituted N-containing heterocyclic residue; $R^3$ is a group capable of forming an anion or a group convertible thereinto; X is a direct bond or a spacer having an atomic length of two or less between the phenylene group and the phenyl group; and n is an integer of 1 or 2) and an oily substance having a lower melting point, and (2) a further object of the present invention is to provide a method for preparing a stabilized pharmaceutical composition for oral use comprising an effective amount of a compound of the formula (I) having antagonistic action to angiotensin II

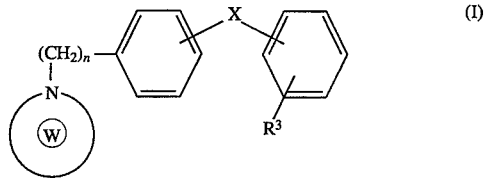

(wherein the ring W is an optionally substituted N-containing heterocyclic residue; $R^3$ is a group capable of forming an anion or a group convertible thereinto; X is a direct bond or a spacer having an atomic length of two or less between the phenylene group and the phenyl group; and n is an integer of 1 or 2) and an oily substance having a lower melting point, which comprises admixing the compound of the formula (I) with an oily substance having a lower melting point and then subjecting the mixture to molding.

DETAILED DESCRIPTION OF THE INVENTION

Referring to the formula (I), examples of a group capable of forming an anion (a group having hydrogen atom capable of being protonated) and a group convertible thereinto represented by $R^3$ include an optionally substituted 5- to 7-membered (preferably 5- to 6-membered) monocyclic heterocyclic residue containing one or more of N, S and O or a group convertible thereinto, for example, carboxyl, tetrazolyl, trifluoromethanesulfonic amide ($-NHSO_2CF_3$), phosphoric acid, sulfonic acid, cyano, lower ($C_{1-4}$) alkoxycarbonyl, and the like. These groups may be protected with, for example, an optionally substituted lower alkyl group (e.g. lower ($C_{1-4}$) alkoxymethyl, optionally substituted arylmethyl, etc.) or an acyl group (e.g. lower ($C_{2-5}$) alkanoyl, optionally substituted benzoyl, etc.). Such groups may include those which are capable of forming anions or are convertible thereinto either chemically or under biological and/or physiological conditions (for example, in vivo reaction such as oxidation-reduction or hydrolysis catalyzed by in vivo enzymes).

Other examples of a group represented by $R^3$ are, like an oxadiazole or thiadiazole ring, those having —NH or —OH group as proton-donor and a carbonyl group, a thiocarbonyl group or sulfinyl group as proton acceptor simultaneously.

$R^3$ also may be tetrazolyl or carboxyl each of which is optionally protected with an optionally substituted lower ($C_{1-4}$) alkyl (e.g. methyl, triphenylmethyl, methoxymethyl, ethoxyethyl, p-methoxybenzyl, p-nitrobenzyl, etc.) or an acyl (e.g. a lower ($C_{2-5}$) alkanoyl, benzoyl, etc.), preferably tetrazolyl group. $R^3$ may be substituted on any of the ortho-, meta- or para-positions, preferably the ortho-position.

X shows that the adjacent phenylene group is bonded to the phenyl group directly or through a spacer with an atomic chain of 2 or less. As the spacer, any one can be exemplified, so long as it is a divalent chain in which the number of atoms constituting the straight chain is 1 or 2, and it may have a side chain. Examples of such spacers include lower ($C_{1-4}$) alkylene,

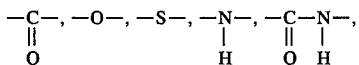

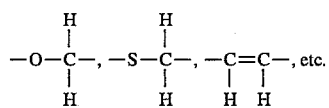

The most preferred X is a chemical bond between the phenylene group and the phenyl group.

n denotes an integer of 1 or 2 (preferably 1).

Among the compounds shown by $R^3$, X and n described above, those shown by the following formula, for example, are preferable:
among

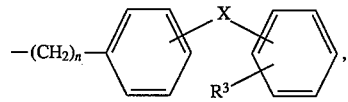

a compound shown by the formula

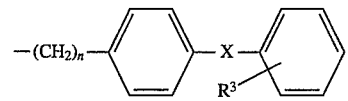

are preferable.

Typical examples of a N-containing heterocyclic residue represented by the ring W are specifically shown as follows. Incidentally, in the following formulae, $R^1$ is hydrogen or an optionally substituted hydrocarbon residue; and Y is a bond, —O—, —S(O)m— (where m denotes 0, 1 or 2) or —N($R^4$)— (where $R^4$ is hydrogen or an optionally substituted alkyl group). Among them, $R^1$ is preferably a lower ($C_{1-5}$) alkyl (preferably a lower ($C_{2-3}$) alkyl) optionally substituted with a hydroxyl group, amino group, halogen or a lower ($C_{1-4}$) alkoxy group; and Y is preferably a bond, —O—, —S— or —N($R^4$)— (wherein $R^4$ stands for hydrogen or a lower ($C_{1-4}$) alkyl).

Examples of the residue represented by the ring W are shown by the formula (III)

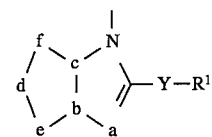

(III)

, wherein a and c forming the heterocyclic residue are independently one or two optionally substituted carbon or hetero atoms; d and f forming the heterocyclic residue are independently one optionally substituted carbon or hetero atom and b and c are independently one optionally substituted carbon or nitrogen atom, and include the following, but are not limited thereto:

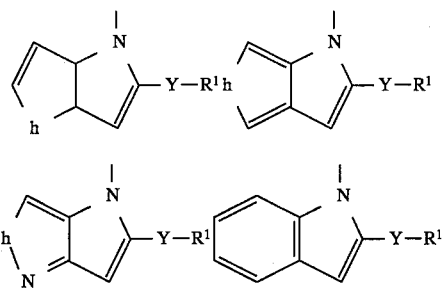

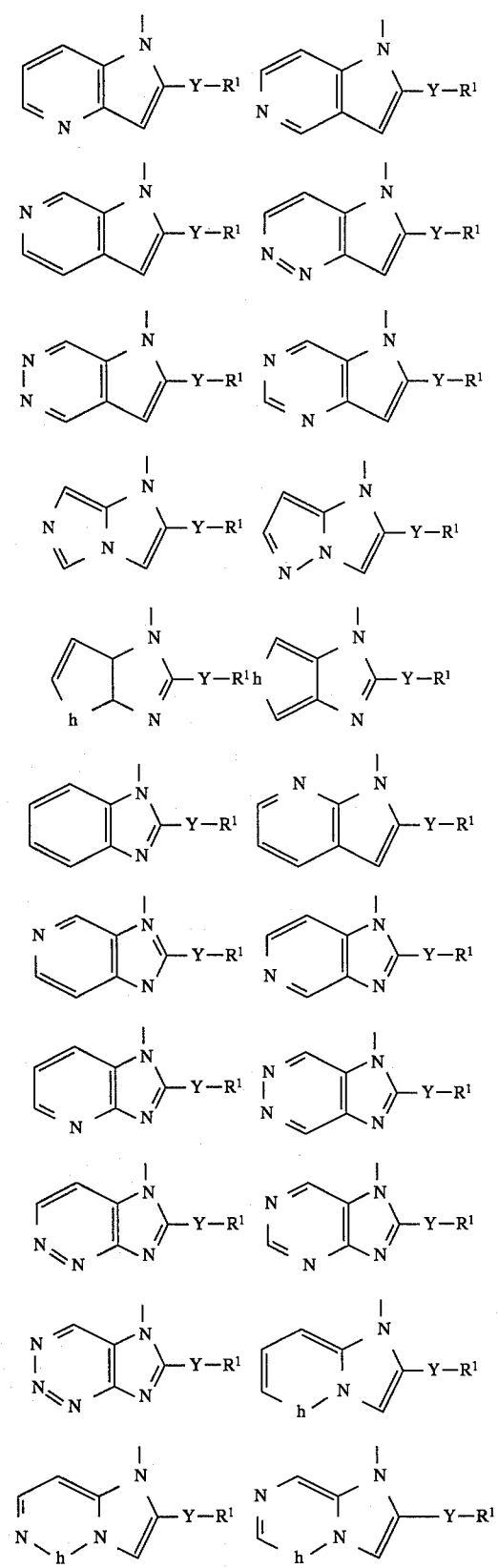
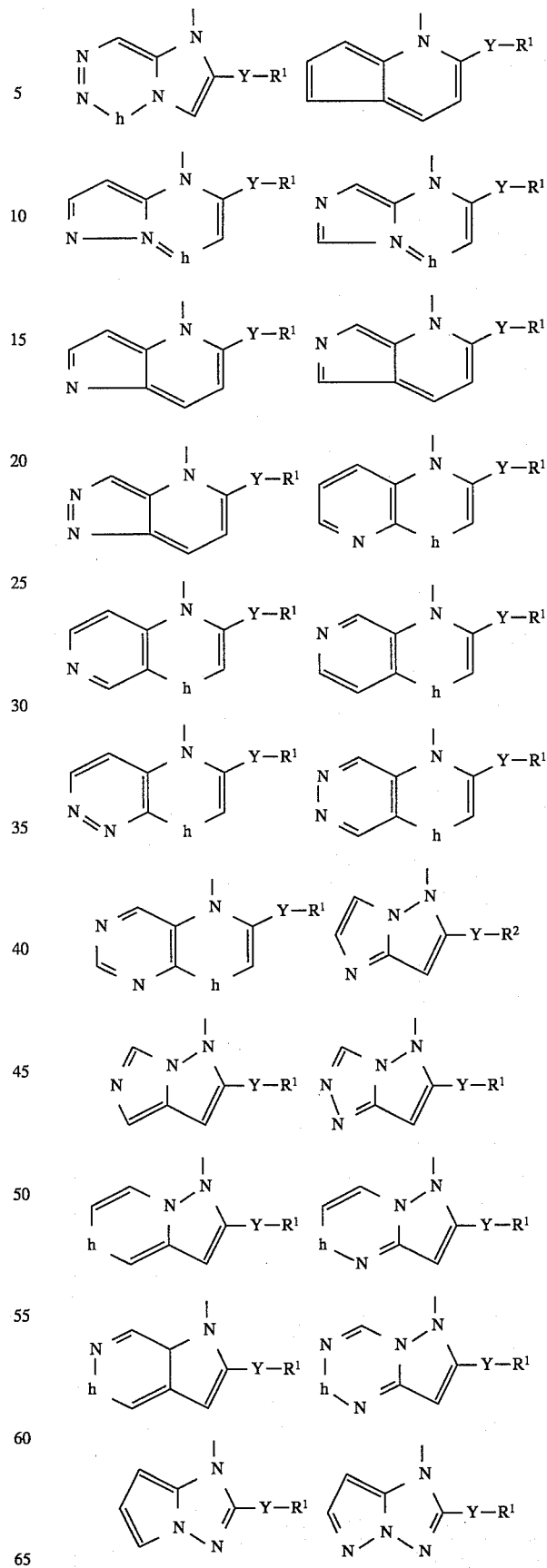

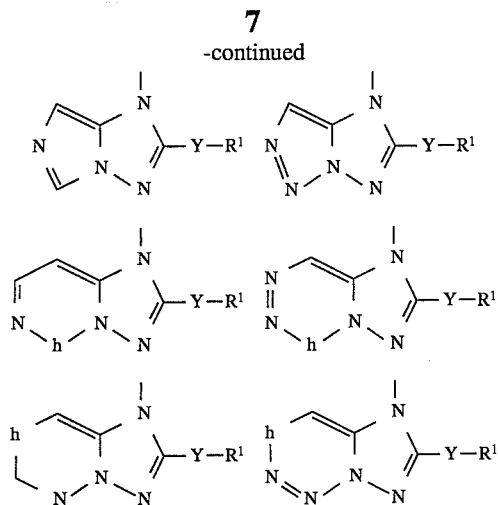

, wherein h is >CH$_2$, >=O, >=S, >S—(O)m, —N(R$^4$)— or —O—; m denotes 0, 1 or 2 and R$^4$ is hydrogen or an optionally substituted lower alkyl (preferably hydrogen or a lower (C$_{1-4}$) alkyl).

Other examples of the residue represented by the ring W are shown by the formula (IV)

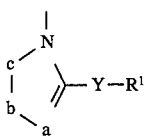 (IV)

, wherein a and b forming the heterocyclic residue are independently one or two optionally substituted carbon or hetero atoms and c is an optionally substituted carbon or hetero atom, and include the following, but are not limited thereto:

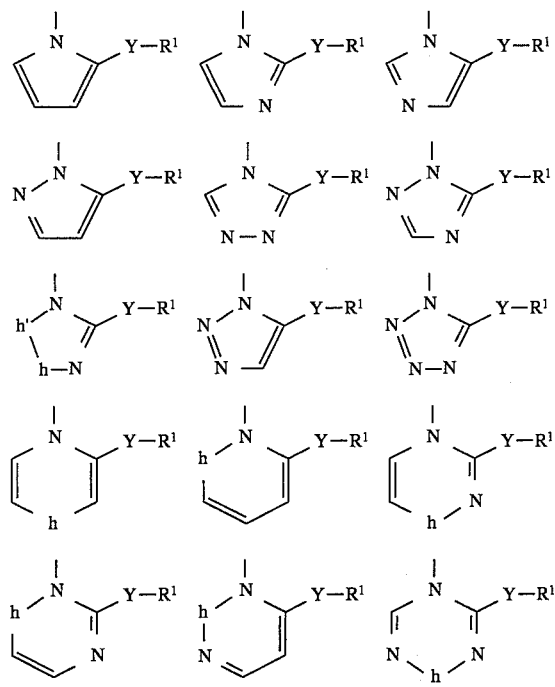

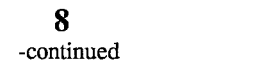
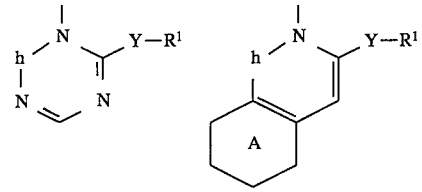
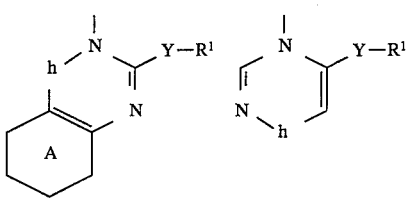
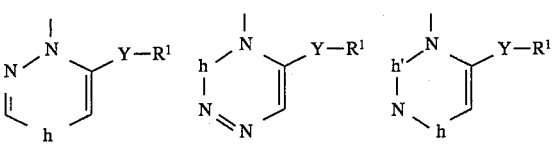

, wherein A is an optionally substituted aromatic hydrocarbon residue, optionally containing a heteroatom, or heterocyclic residue (preferably aromatic hydrocarbon residue such as phenyl), h and h' each shows >CH$_2$, >=O, >=S, >S—(O)$_m$, —N(R$^4$)— and —O— and, m and R$^4$ are of the same meaning as defined above.

The heterocyclic residue represented by the above-mentioned formula (III) may optionally be substituted, besides the group represented by Y—R$^4$, with a group represented by R$^2$ (e.g. a group capable of forming an anion or a group convertible thereinto). The substitution position of R$^2$ is preferably the position of the f atom in the formula (III).

Examples of the group R$^2$ capable of forming anion or a group convertible thereinto include optionally esterified or amidated carboxyl, tetrazolyl, trifluoromethanesulfonic acid amide (—NHSO$_2$CF$_3$), phosphoric acid and sulfonic acid. These groups may optionally be protected by an optionally substituted lower alkyl group or acyl group, and may be any one as long as they are capable of forming anion under biological or physiological conditions (for example, an in vivo reaction such as oxidation, reduction or hydrolysis by in vivo enzymes) or chemically.

Examples of optionally esterified or amidated carboxyl represented by R$^2$ include groups represented by the formula —CO—D [wherein D stands for hydroxyl group, optionally substituted amino (e.g. amino, N-lower (C$_{-4}$) alkylamino, and N,N-di-lower (C$_{4-4}$) alkylamino) or optionally substituted alkoxy {e.g. a lower (C$_{-6}$) alkoxy group, whose alkyl moiety is optionally substituted with hydroxyl group, optionally substituted amino (e.g. amino, dimethylamino, diethylamino, piperidino and morpholino), halogen, lower (C$_{-6}$) alkoxy, lower (C$_{1-6}$) alkylthio or optionally substituted dioxolenyl (e.g. 5-methyl-2-oxo-1,3-dioxolen-4-yl), or groups represented by the formula —O—CH(R$^4$)-OCOR$_5$ [wherein R$^6$ stands for hydrogen, a C$_{1-6}$ straight-chain or branched lower alkyl group (e.g. methyl, ethyl, n-propyl, isopropyl, n-butyl, isobutyl, t-butyl, n-pentyl, isopentyl and neopentyl), a C$_{2-6}$ straight-chain or branched lower alkenyl group or a C$_{3-8}$ cycloalkyl group (e.g. cyclopentyl, cyclohexyl and cycloheptyl), and R$^5$ stands for a C$_{1-6}$ straight-chain or branched lower alkyl group (e.g. methyl, ethyl, n-propyl, isopropyl, n-butyl, sec-butyl, t-butyl, n-pentyl, isopentyl and neopentyl), a C$_{2-6}$ straight-chain or branched lower alkenyl group, a C$_{3-8}$ cycloalkyl group (e.g. cyclopentyl, cyclohexyl and cycloheptyl), a $C_{1-3}$ lower alkyl group substituted with $C_{3-8}$ cycloalkyl (e.g. cyclopentyl, cyclohexyl and cycloheptyl) or an optionally substituted aryl group such as phenyl (e.g. benzyl, p-chlorobenzyl, phenethyl, cyclopentylmethyl and cyclohexylmethyl), a $C_{2-3}$ lower alkenyl group optionally substituted with $C_{3-8}$ cycloalkyl or an optionally substituted aryl group such as phenyl (e.g. cinnamyl, etc. having alkenyl moiety such as vinyl, propenyl, allyl and isopropenyl), an aryl group such as optionally substituted phenyl (e.g. phenyl, p-tolyl and naphtyl), a $C_{1-6}$ straight-chain or branched lower alkoxy group (e.g. methoxy, ethoxy, n-propoxy, isopropoxy, n-butoxy, isobutoxy, sec-butoxy, n-pentyloxy, isopentyloxy and neopentyloxy), a $C_{2-8}$ straight-chain or branched lower alkenyloxy group (e.g. allyloxy and isobutenyloxy),a $C_{3-8}$ cycloalkyloxy group (e.g. cyclopentyloxy, cyclohexyloxy, and cycloheptyloxy), a $C_{1-3}$ lower alkoxy group substituted with $C_{3-8}$ cycloalkyl (e.g. cyclopentyl, cyclohexyl and cyloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), a $C_{2-3}$ lower alkenyloxy group substituted with $C_{3-8}$ cycloalkyl (e.g. cyclopentyl, cyclohexyl and cycloheptyl) or an aryl group such as optionally substituted phenyl (e.g. cinnamyloxy having an alkenyloxy moiety such as vinyloxy, propenyloxy, allyloxy and isopropenyloxy) and an aryloxy group such as optionally substituted phenoxy (e.g. phenoxy, p-nitrophenoxy and naphthoxy)]}}. And, examples of the substituent represented by $R^2$ may also include a group capable of forming anion or a group convertible thereinto (e.g. tetrazolyl, trifluoromethanesulfonic acid amide, phosphoric acid or sulfonic acid optionally protected with alkyl (e.g. a lower $(C_{1-4})$ alkyl) or acyl (e.g. lower $(C_{2-5})$ alkanoyl and optionally substituted benzoyl).

Examples of the substituent $R^2$ include —COOH and a salt thereof, —COOMe, —COOEt, —COOtBu, —COOPr, pivaloyloxymethoxycarbonyl, 1 -(cyclohexyloxycarbonyloxy)ethoxycarbonyl, 5-methyl-2 -oxo-1,3-dioxolen-4-yl-methoxycarbonyl, acetoxymethyloxycarbonyl, propionyloxymethoxycarbonyl, n-butyryloxymethoxycarbonyl, isobutyryloxymethoxycarbonyl, 1 -(ethoxycarbonyloxy)ethoxycarbonyl, 1 -(acetyloxy)ethoxycarbonyl, 1 -(isobutyryloxy)ethoxycarbonyl, cyclohexylcarbonyloxymethoxycarbonyl, benzoyloxymethoxycarbonyl, cinnamyloxycarbonyl and cyclopentylcarbonyloxymethoxycarbonyl. As such groups as above, any one capable of forming anion (e.g. COO⁻ and its derivatives) or a group convertible thereinto under biological or physiological conditions (e.g. in vivo reaction such as oxidation, reduction or hydrolysis catalyzed by in vivo enzymes) or chemically is mentioned. $R^2$ may be carboxyl or a prodrug thereof. $R^2$ may also be groups convertible into an anion in vivo, for example, biologically or chemically.

$R^2$ is preferably a group represented by the formula —CO—D—, wherein D is hydroxyl or a lower $(C_{1-4})$ alkoxy whose alkyl portion is optionally substituted with hydroxyl, amino, halogen, a lower $(C_{2-6})$ alkanoyloxy (acetyloxy, pivaloyloxy, etc.), 1-lower $(C_{1-6})$ alkoxycarbonyloxy (e.g. methoxycarbonyloxy, ethoxycarbonyloxy, cyclohexyloxycarbonyloxy, etc.) or a lower $(C_{1-4})$ alkoxy.

The heterocyclic residue represented by the formula (III) may optionally have, besides the groups represented by Y—$R^1$ and $R^2$, further substituents as exemplified by halogen (e.g. F, $C_{1-4}$ and Br), nitro, cyano, a lower $(C_{1-4})$ alkyl, a lower $(C_{1-4})$ alkoxy, an optionally substituted amino group [e.g. amino, N-lower $(C_{1-4})$ alkylamino (e.g. methylamino), N,N-di-lower $(C_{1-4})$ alkylamino (e.g. dimethylamino), N-arylamino (e.g. phenylamino), alicyclic amino (e.g. morpholino, piperidino, piperazino and N-phenylpiperazino)], a group represented by the formula —CO—D'—, wherein D' is hydroxyl group or a lower $(C_{1-4})$ alkoxy whose alkyl portion is optionally substituted with hydroxyl, a lower $(C_{1-4})$ alkoxy, a lower $(C_{2-6})$ alkanoyloxy (acetyloxy, pivaloyloxy, etc.) or a lower $(C_{1-6})$ alkoxycarbonyloxy (e.g. methoxycarbonyloxy, ethoxycarbonyloxy, cyclohexyloxycarbonyloxy, etc.) and tetrazolyl, trifluoromethanesulfonic acid amide, phosphoric acid or sulfonic acid, each optionally protected with alkyl (e.g. lower $(C_{1-4})$ alkyl) or acyl (e.g. lower $(C_{2-5})$ alkanoyl and optionally substituted benzoyl). One or two of these substituents may optionally be substituted simultaneously on optional positions of the ring.

Among the compounds represented by the formula (III), as condensed heterocyclic ring, preferable examples are

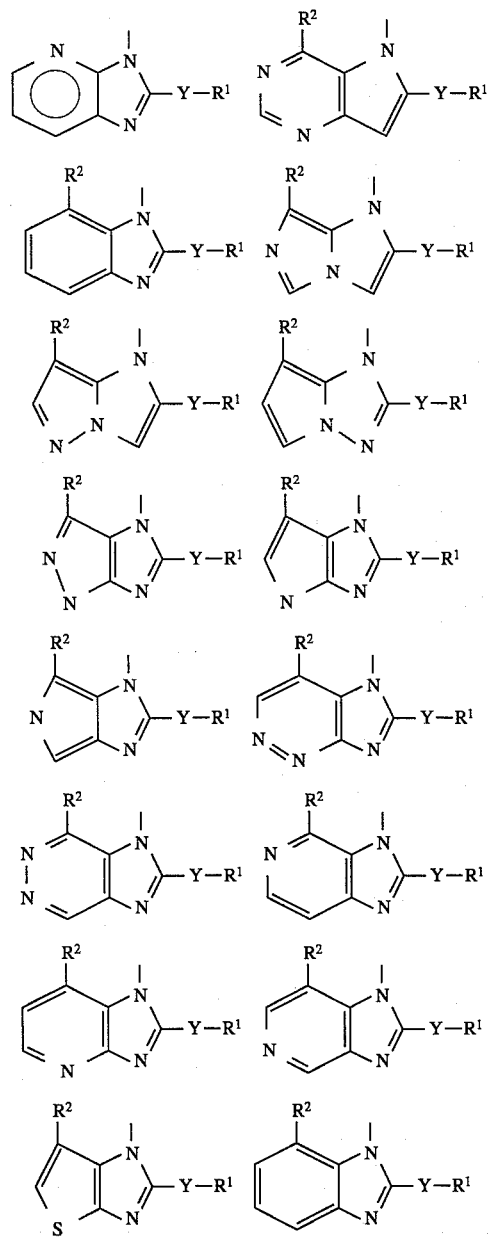

-continued

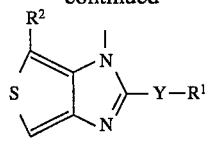

, wherein Y—R⁴ and R² are of the same meaning as defined above, namely the condensed heterocyclic ring is preferably a ring of benzimidazole, thioimidazole or imidazopyridine (preferably benzimidazole and thioimidazole).

Among the compounds represented by the above mentioned formula (I), preferable ones are represented by the formula

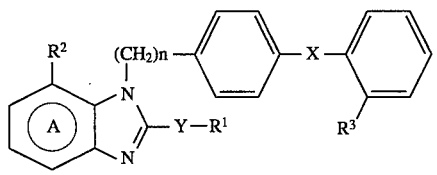

, wherein the ring A is a benzene ring which may have, besides the group represented by $R^2$, further substituents; $R^1$ is hydrogen or an optionally substituted hydrocarbon residue; $R^3$ is a group capable of forming anion or a group convertible thereinto; X shows that phenylene group and phenyl group are bonded directly or through a spacer having two or less atomic chain; $R^2$ is an optionally esterified carboxyl group; Y is a bond, —O—, —S(O)m— (where m denotes 0, 1 or 2) or —N(R⁴)— (where $R^4$ is hydrogen or an optionally substituted alkyl group); and n denotes an integer of 1 or 2] or their salts. More specifically, among the benzimidazole-7-carboxylic acid derivatives disclosed in the official gazette of EP Publication No. 0425921 A1 or the official gazette of EP Publication No. 0459136 A1, any of the crystallized ones can be employed. Among them, preferable are a compound (I'), which are the compound (I) wherein $R^1$ is a lower $C_{1-5}$ alkyl (preferably a lower ($C_{2-3}$) alkyl) optionally substituted with hydroxyl group, amino group, halogen or a lower ($C_{1-4}$) alkoxy group; $R^2$ is a group represented by the formula —CO—D, [wherein D is hydroxyl or a lower ($C_{1-4}$) alkoxy whose alkyl portion is optionally substituted with hydroxyl, amino, halogen, a lower ($C_{2-6}$) alkanoyloxy (e.g. acetyloxy, pivaloyloxy, etc.), 1-lower ($C_{1-6}$) alkoxycarbonyloxy (e.g. methoxycarbonyloxy, ethoxycarbonyloxy, cyclohexyloxycarbonyloxy, etc.) or a lower ($C_{1-4}$) alkoxy]; The ring A is a benzene ring which may have, besides the group represented by $R^2$ further substituents selected from the class of halogen (e.g. F, Cl, Br, etc.), a lower ($C_{1-4}$) alkyl, a lower ($C_{1-4}$) alkoxy, nitro, a group represented by the formula —CO—D'—, wherein D' is hydroxyl group or a lower ($C_{1-4}$) alkoxy whose alkyl portion is optionally substituted with hydroxyl, a lower ($C_{1-4}$) alkoxy, a lower ($C_{2-6}$) alkanoyloxy (e.g. acetyloxy, pivaloyloxy, etc.) or a 1 -lower ($C_{1-6}$) alkoxycarbonyloxy (e.g. methoxycarbonyloxy, ethoxycarbonyloxy, cyclohexyloxycarbonyloxy, etc.), and amino optionally substituted with a lower ($C_{1-4}$) alkyl, preferably a substituent such as a lower ($C_{1-4}$) alkyl, halogen etc., more preferably, a benzene ring which has no substituents but those shown by $R^2$; Y is a bond, —O—, —S— or N(R⁴)—, wherein $R^4$ is hydrogen or a lower ($C_{1-4}$) alkyl: $R^3$ is tetrazolyl or carboxyl each of which is optionally protected with an optionally substituted lower ($C_{1-4}$) alkyl (e.g. methyl, triphenylmethyl, methoxymethyl, ethoxyethyl, p-methoxybenzyl, p-nitrobenzyl, etc.) or an acyl (a lower ($C_{2-5}$) alkanoyl, benzoyl, etc.); n denotes 1; and X is a bond.

Among the above-mentioned formula (I), (±)-1 -(cyclohexyloxycarbonyloxy)ethyl 2-ethoxy-1[[2'-( 1H-tetrazol-5-yl)biphenyl-4-yl]methyl]-1H-benzimidazole-7 -carboxylate (hereinafter sometimes called the formula (V). cf. the following structural formula) is preferably employed, namely a compound (I), wherein $R^1$ stands for ethyl; $R^2$ stands for 1-(cyclohexyloxycarbonyloxy)-ethoxycarbonyl; the ring A stands for a benzene ring having no further substituent but the group shown by $R^2$; Y stands for —O—; $R^3$ stands for tetrazolyl; n denotes 1; and X stands for a bond. While the crystal form of these compounds is not critical, stable C-type crystals described in the Experimental Example 1 in the official gazette of EP Publication No. 0459136A1 are especially desirable in the case of the formula (V).

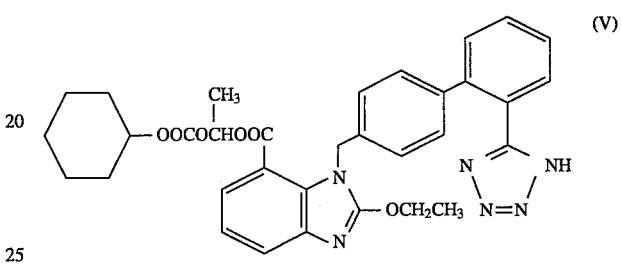

Among the compounds represented by the formula (I) having antagonistic action to angiotensin II, those with a crystalline structure having the melting point of 100° to 200° C., especially 130° to 180° C. are conveniently employed from the viewpoint of stability.

Among the oily substances, any one can be used, so long as it is oily and has a melting point of about 20° to 90° C., preferably 20° to 60° C. and exerts no undesirable influence on the active component. The above oily substances may be more evenly admixed with the active component in preparation of pharmaceutical compositions for oral use of the present invention so that more stable compositions is produced, as compared with use of an oily substance having a higher melting point. Furthermore, among them, any one may be soluble or unsoluble in water. Here, an example of the oily substances which is soluble in water is a polymer of alkylene oxide, as mentioned below. Examples of these substances include hydrocarbons, higher fatty acids, higher alcohols, fatty acid esters of polyhydric alcohols, higher alcohol ethers of polyhydric alcohols, and polymers or copolymers of alkylene oxide. Among them, fatty acid esters of polyhydric alcohols, higher alcohol ethers of polyhydric alcohols, polymers or copolymers of alkylene oxide, especially polymers of alkylene oxide, are preferably employed.

Examples of hydrocarbons include $C_{17-50}$ n-alkane such as n-heptadecane, n-octadecane, n-nonadecane, n-eicosane, n-heneicosane, n-docosane, n-tricosane, n-tetracosane, n-pentacosane, n-triacontane, n-pentatriacontane, n-tetracontane and n-pentacontane, as well as a mixture of them (petrolatum, paraffin wax, microcrystalline wax, etc.)

Examples of higher fatty acids include capric acid, lauric acid, myristic acid, palmitic acid, stearic acid, arachidinic acid, behenic acid, lignoceric acid, cerotic acid and a mixture of them, as well as higher fatty acid collectable from natural fatty acid.

Examples of higher alcohols include lauryl alcohol, myristyl alcohol, cetyl alcohol, stearyl alcohol, aralkyl alcohol and a mixture of them, as well as higher alcohol collectable from natural oil.

Examples of fatty acid esters of polyhydric alcohols include esters formed by esterification of an alcohol having two or more hydroxyl groups in the molecule (for example, alkylene glycols such as ethylene glycol and propylene glycol; polyalkylene glycols such as polyethylene glycol, polypropylene glycol or copolymers of them; sugars such as sorbitol, sucrose and raffinose; intramolecular dehydrates such as 1,5-sorbitan, 1,4-sorbitol and 3,6-sorbitan; glycerin, diethanolamine, pentaerythritol, etc.) with a fatty acid (for example, acetic acid, propionic acid, butyric acid, pelargonic acid, capric acid, undecylic acid, lauric acid, tridecylic acid, myristic acid, pentadecylic acid, palmitic acid, heptadecylic acid stearic acid, nonadecanoic acid undecylenic acid, oleic acid, elaidic acid, sorbic acid, linoleic acid, linolenic acid, arachidonic acid, stearolic acid, etc.), more specifically, sorbitan fatty acid esters having a molecular weight of 400 to 900, such as sorbitan monostearate, sorbitan tristearate, sorbitan monooleate, sorbitan sesquioleate or sorbitan monopalmitate; polyoxyalkylene sorbitan fatty acid esters having a molecular weight of 1000 to 1500, such as polyoxyethylene sorbitan tristearate, polyoxyethylene sorbitan monooleate or polyoxyethylene sorbitan tripalmitate; polyoxyalkylene sorbitol fatty acid esters, such as polyoxyethylene sorbitol hexastearate, polyoxyethylene sorbitol hexaoleate, polyoxyethylene sorbitol tristearate or polyoxyethylene sorbitol tetralaurate; polyoxyalkylene sorbitot bees wax derivatives such as polyoxyethylene sorbitol bees wax derivatives; polyoxyalkylene hydrous lanolin derivatives such as polyoxyethylenehydrous lanolin derivatives; propylene glycol fatty acid esters having a molecular weight of 200 to 700 such as propylene glycol monopalmitate, propylene glycol monostearate, propylene glycol dilaurate, propylene glycol dimyristate, propylene glycol dipalmitate or propylene glycol distearate; alkylene glycol fatty acid esters including ethylene glycol fatty acid ester having a molecular weight of 500 to 1200, such as ethylene glycol monolaurate, ethylene glycol palmitate, ethylene glycol margarate, ethylene glycol stearate, ethylene glycol dilaurate, ethylene glycol dimyristate, ethylene glycol dipalmitate or ethylene glycol dimargarate; polyoxyethylene castor oil derivatives having a molecular weight of 3500 to 4000, such as polyoxyethylene castor oil derivatives; polyoxyalkylene fatty acid esters having a molecular weight of 1900 to 2200, such as polyoxyethylene stearate, polyoxyethylene oleate polyoxyethylene palmitate or polyoxyethylene linolate; glycerine monofatty acid esters having a molecular weight of 300 to 600, such as glycerine monoacetate, glycerine monopropionate, glycerine monostearate, glycerine monooleate, glycerine monopalmitate or glycerine monolinolate; and sucrose fatty acid esters having a molecular weight of 400 to 1300, such as sucrose monolaurate, sucrose monomyristate, sucrose monopalminate, sucrose monostearate, sucrose trimyristate, sucrose tripalmitate or sucrose tristearate.

Examples of higher alcohol ethers of polyhydric alcohols include ethers formed by etherification of a polyhydric alcohol (set forth as alcohol components of the fatty acid ester of polyhydric alcohol mentioned above) with a higher fatty acid alcohol (for example, cetyl alcohol, stearyl alcohol, oleyl alcohol, octyl alcohol or decyl alcohol), more specifically, polyoxyethylene higher alcohol ethers such as polyoxyethylene lauryl alcohol ether, polyoxyethylene cetyl alcohol ether, polyoxyethylene stearyl alcohol ether, polyoxyethylene oleyl alcohol ether, polyoxyethylene octyl alcohol ether or polyoxyethylene decyl alcohol ether; and polyoxypropylene polyoxyethylene higher alcohol ethers such as polyoxypropylene polyoxyethylene cetyl alcohol ether, polyoxypropylene polyoxyethylene stearyl alcohol ether, polyoxypropylene polyoxyethylene oleyl alcohol ether, polyoxypropylene polyoxyethylene octyl alcohol ether or polyoxypropylene polyoxyethylene lauryl alcohol ether are generally used.

As the polymer of alkylene oxide, use is made of those having a molecular weight of 1,000 to 10,000 (e.g. polyethylene glycol 6000). Examples of the alkylene oxide include ethylene oxide, propylene oxide, trimethylene oxide and tetrahydrofuran (preferably ethylene oxide).

As the copolymer of alkylene oxide, use is made of copolymers of two or more species of the above-mentioned alkylene oxides, having a molecular weight of 1,000 to 10,000.

These substances may be used singly or as a mixture of two or more of them.

These substances are added to the active component in a solid or liquid state.

The present invention is more conveniently applied to a solid composition (e.g. granules and tablets, preferably tablets) prepared by molding (e.g. granulation or molding under elevated pressure).

Preparation of a solid composition of the present invention is usually conducted by incorporating such an oily substance having a lower melting point into the active component, followed by subjecting the mixture to molding. The incorporation is conducted by a method conventionally employed in the field of pharmaceutical preparations, for example, mixing, massing, kneading, sieving and stirring. For example, an oily substance having a lower melting point is directly added to the active component and to make a mixture (addition in powdery state), or a solvent is added the mixture, followed by conventional granulating and drying. Alternatively, an oily substance having a lower melting point is dissolved in a suitable solvent, then the solution is mixed with the active component, followed by conventional kneading, granulating and drying (addition in liquid state). Further, a liquid material containing an oily substance having a lower melting point and a liquid material containing the active component can be independently sprayed onto a powdery material such as an excipient, followed by mixing the resultant material. In the case of "addition in liquid state", any solvent which does not exert undesirable influence on the effective component, for example, water, dimethylformamide, acetone, ethanol, propyl alcohol, isopropyl alcohol, butyl alcohol, methylene chloride and trichloroethane, can be employed. After completing the blending, the material is subjected to a conventional molding process under elevated pressure to prepare tablets containing the active component. The molding under elevated pressure means that a material is compressed under elevated pressure into a desired form, and it refers to, most generally, tabletting. Incorporation of such an oily substance having a lower melting point as described above serves to minimize crystalline disorder possibly caused in the steps of kneading, granulating and molding under elevated pressure, and is considered to further serve advantageously to improve the moldability and to lower the pressure to be elevated. And, in the method of preparing the composition of this invention, a variety of additives to be employed for solid compositions can be added in an adequate step. These additives are exemplified by excipients such as crystalline cellulose (e.g. Avicel PH 101 (manufactured by Asahi Chemical Industry Co., Ltd.)), carboxymethyl cellulose calcium, corn starch, wheat starch, lactose, sucrose, glucose, calcium sulfate, calcium phosphate or sodium chloride, binders such as gum arabic, gelatin, methyl cellulose, polyvinyl pyrrolidone, hydroxypropyl cellulose (hereinafter sometimes abbreviated as HPC) or hydroxypropylmethyl cellulose, lubricants such as magnesium stearate, talc, synthetic aluminum silicate, sodium lauryl sulfate, boric acid, magnesium oxide or paraffin, colorants, flavoring agents, odor-improving agents, etc. Incidentally, in the case of using such a crystalline compound whose specific gravity is relatively small as the formula (V), it is desirable to have the compound dispersed in advance in a thick liquid containing such a binder as HPC and water. Furthermore, the composition of this invention may be prepared into coated tablets as well.

The coating may be conducted by a per se known method. As coating agents, use is made of conventional ones (e.g. hydroxypropylmethyl cellulose, hydroxypropyl cellulose, methyl cellulose and polyvinyl pyrrolidone), and as auxiliary agents for coating, use is made of, for example, polyethylene glycol 6000, polysorbate (e.g. Tween 80), titanium oxide, and pigments such as red iron oxide.

In the stabilized pharmaceutical composition for oral use in the present invention prepared by admixing an oily substance having a lower melting point with the active component, the amount of the oily substance is 0.005 to 0.15 weight, preferably 0.01 to 0.1 weight, more preferably 0.02 to 0.05 weight per 1 weight of the composition, and the amount of the active component is 0.001 to 0.15 weight, preferably 0.007 to 0.09 weight, more preferably 0.015 to 0.04 weight per 1 weight of the composition.

Also, the stabilized pharmaceutical composition for oral use in the present invention is desirable to disintegrate in an aqueous solution with 30 minutes.

In the orally administrable pharmaceutical composition thus prepared by incorporating an oily substance having a lower melting point into the active component, decomposition with time possibly caused by compression can be suppressed to provide a stable composition. In the case of using the pharmaceutical composition of this invention for the therapy of hypertension, cardiac diseases, cerebral apoplexy or renal diseases of mammals (e.g. man, dog, rabbit or rat), it can be administered orally as tablets. The dosage ranges from about 1 to 50 mg, preferably from about 2 to 30 mg per day in terms of the active component (e.g. the compound of the formula (I) having antagonistic action to angiotensin II).

[WORKING EXAMPLES]

For a more complete understanding of the instant invention, reference is made to the following illustrative examples, although it should be clearly understood that the invention is not be limited thereto.

Example 1

In a fluid-bed granulator (Powrex, FD-3S), in accordance with the following formulation, polyethylene glycol 6000 as the oily substance having a lower melting point was mixed with other ingredients including the compound of the formula (I) having antagonistic action to angiotensin II (the active component). Onto the mixture was sprayed an aqueous solution of hydroxypropyl cellulose as the binder, which was granulated and dried to give granules. To the granules was added carboxylmethylcellulose calcium and magnesium stearate, and the mixture was tabletted by a tablet machine (Kikusui Seisakusho, Correct 19K) using a punch (7.0 mm in diameter) of bevelled edge at a weight of 130 mg under a pressure of 2.0 ton/cm². The tablets thus prepared were stored at 50° C. of 40° C. and subjected to stability test.

| Formulation | | |
|---|---|---|
| Materials | Sample A | Control B |
| the formula (V) | 1.0 mg | 1.0 mg |
| Lactose | 93.0 | 99.0 |
| Corn starch | 20.0 | 20.0 |
| Polyethylene glycol 6000 | 6.0 | — |
| Hydroxypropyl cellulose | 4.0 | 4.0 |
| (water) | (0.135 ml) | (0.135 ml) |
| Sub-total | 124.0 mg | 124.0 mg |
| Carboxymethylcellulose-calcium | 5.6 | 5.6 |
| Magnesium stearate | 0.4 | 0.4 |
| Total | 130.0 mg | 130.0 mg |

| Results of stability test | | |
|---|---|---|
| Item | Sample A | Control B |
| At the initial time of test (hereinafter simply written as "initial") | (100) | (100) |
| Residual ratio after storing at 50° C. for 4 weeks | 99.3 | 89.7 |
| Residual ratio after storing at 40° C. for 8 weeks | 99.8 | 94.8 |

The stability test was conducted by determining the content of the formula (V) after storing the respective periods by liquid chromatography, and the residual ratios were shown by percent. As the control, the composition (B) containing no stabilizing agent (an oily substance having a lower melting point) was employed, and the test was conducted by comparing it with the composition (A) containing polyethylene glycol 6000 as the oily substance having a lower melting point. As is clear from the test results, the composition of this invention is excellent in stability as compared with the control.

Example 2

In a fluid-bed granulator (Glatt WSG-15), in accordance with the same formulation as in Example 1, polyethylene glycol 6000 as the oily substance having a lower melting point was dissolved in water, in which the formula (V) was dispersed, then the dispersion was sprayed on a powder mixture of lactose and corn starch. The resultant material was further sprayed with an aqueous solution of hydroxypropyl cellulose, which was granulated and dried to give granules. The granules were mixed with carboxylmethylcellulose calcium and magnesium stearate, and the mixture was tabletted by a tablet machine using a punch (7.0 mm in diameter) of bevelled edge at a weight of 130 mg under a pressure of 2.0 ton/cm².

| Test results of stability | | |
|---|---|---|
| Item | Sample A | Control B |
| Initial | (100) | (100) |
| Residual ratio after storing at 50° C. for one week | 99.0 | 89.0 |
| Residual ratio after storing at 40° C. for 4 weeks | 99.8 | 91.1 |

From the test results, it is understood that, in the composition of this invention, the formula (V) is remarkably stable as compared with that in the control.

Example 3

In a fluid-bed granulator (Powrex FD-5S), in accordance with the same formulation as in Example 1, an aqueous solution of polyethylene glycol 6000 as the oily substance having a lower melting point was sprayed onto a powder mixture of lactose and corn starch. The resultant material was further sprayed with a dispersion of the formula (V) in an aqueous solution of hydroxypropyl cellulose, which was granulated and dried to give granules. The granules were mixed with magnesium stearate and carboxylmethylcellulose calcium, and the mixture was tabletted by a tablet machine (Kikusui Seisakusho, Correct 19K) using a punch of shallow concave (7.0 mm in diameter) at a weight of 130 mg under a pressure of 2.0 ton/cm$^2$.

Further, in accordance with the following formulation of aqueous coating tablets, the aqueous coating (5 mg) was performed by Accelacoater (Manesty Co., Ltd., Great Britain) using hydroxypropylmethyl cellulose.

| Formulation | |
|---|---|
| Materials | per tablet |
| Core tablet | 130.0 mg |
| Hydroxypropylmethyl cellulose | 3.50 mg |
| Polyethylene glycol 6000 | 0.75 mg |
| Titanium oxide | 0.75 mg |
| (water) | (0.05 ml) |
| Total | 135.0 mg |

| Results of stability test | | |
|---|---|---|
| Item | Sample A | Control B |
| Initial | (100) | (100) |
| Residual ratio after storing at 50° C. for 4 weeks | 99.4 | 88.4 |
| Residual ratio after storing at 40° C. for 8 weeks | 100.0 | 90.2 |

From the results of the test, it is understood that, in the composition of this invention, the formula (V) is remarkably stable as compared with that in the control.

Example 4

In a granulator equipped with stirrer (Powrex, vertical granulator VG10), the formula (V) was dispersed in an aqueous solution of polyethylene glycol 6000 as the oily substance having a lower melting point and HPC. This dispersion was added to a powder mixture of lactose and corn starch, which was granulated and dried to give granules, followed by addition of magnesium stearate and carboxylmethylcellulose calcium. The mixture was tabletted by a tablet machine using a punch of bevelled edge (7.0 mm in diameter) at a weight of 130 mg under a pressure of 2.0 ton/cm$^2$.

| Formulation | | |
|---|---|---|
| Materials | Sample A | Control B |
| the formula (V) | 10.0 mg | 10.0 mg |
| Lactose | 84.0 | 90.0 |
| Corn starch | 20.0 | 20.0 |
| Polyethylene glycol 6000 | 6.0 | — |
| Hydroxypropyl cellulose | 4.0 | 4.0 |
| (water) | (0.024 ml) | (0.024 ml) |
| Sub-total | 124.0 mg | 124.0 mg |
| Carboxylmethylcellulose-calcium | 5.6 | 5.6 |
| Magnesium stearate | 0.4 | 0.4 |
| Total | 130.0 mg | 130.0 mg |

| Results of stability test | | |
|---|---|---|
| Item | Sample A | Control B |
| Initial | (100) | (100) |
| Residual ratio after storing at 50° C. for 4 weeks | 99.1 | 87.2 |
| Residual ratio after storing at 40° C. for 8 weeks | 99.5 | 89.7 |

From the results of the test, it is understood that, in the composition of this invention, the formula (V) is remarkably stable as compared with that in the control.

Example 5

In substantially the same manner as in Example 1, tablets were prepared under the formulation as shown in the following Table 1. These tablets were subjected to the test of stability in substantially the same manner as in Example 1. The results are shown in Table 2.

[TABLE 1]

| | Formulation | | | | |
|---|---|---|---|---|---|
| | Samples | | | | Control |
| Materials | A | B | C | D | E |
| the formula (V) | 1.0 mg | 1.0 mg | 1.0 mg | 1.0 mg | 1.0 mg |
| Lactose | 98.0 | 89.0 | 93.0 | 93.0 | 99.0 |
| Corn starch | 20.0 | 20.0 | 20.0 | 20.0 | 20.0 |
| Stearyl alcohol | 1.0 | 10.0 | — | — | — |
| Sucrose fatty acid ester | — | — | 6.0 | — | — |
| Sorbitan fatty acid ester | — | — | — | 6.0 | — |
| Hydroxy propyl cellulose | 4.0 | 4.0 | 4.0 | 4.0 | 4.0 |
| (Water) | (0.135 ml) | (0.135) | (0.135) | (0.135) | (0.135) |
| Sub-total | 124.0 mg | 124.0 | 124.0 | 124.0 | 124.0 |
| Carboxymethyl cellulose | 5.6 | 5.6 | 5.6 | 5.6 | 5.6 |

[TABLE 1]-continued

| Materials | Formulation | | | | |
|---|---|---|---|---|---|
| | Samples | | | | Control |
| | A | B | C | D | E |
| calcium Magnesium stearate | 0.4 | 0.4 | 0.4 | 0.4 | 0.4 |
| Total | 130.0 mg | 130.0 | 130.0 | 130.0 | 130.0 |

[TABLE 2]

| Item | Results of stability test | | | | |
|---|---|---|---|---|---|
| | Samples | | | | Control |
| | A | B | C | D | E |
| Initial | (100) | (100) | (100) | (100) | (100) |
| Residual ratio after storing at 50° C. for 4 weeks | 99.0 | 99.4 | 98.9 | 99.1 | 89.7 |
| Residual ratio after storing at 40° C. for 4 weeks | 99.2 | 100.0 | 99.3 | 99.6 | 94.8 |

From the above test results, it is understood that the composition of this invention in which an oily substance having a relatively low melting point is excellent in the stability of the formula (V) contained therein.

Example 6

In substantially the same manner as in Example 1, tablets can be prepared under the formulations as shown in the following Table 3.

[TABLE 3]

| Materials | Formulation | | | |
|---|---|---|---|---|
| | Samples | | | |
| | A | B | C | D |
| 2-ethoxy-1-[[2'-(1H-tetrazol-5-yl)biphenyl-4-yl]methyl]benzimidazole-7-carboxylic acid | 1.0 mg | — | — | — |
| 2-butyl-1-[[2'-(1H-tetrazol-5-yl)biphenyl-4-yl]methyl]benzimidazole-7-carboxylic acid | — | 1.0 | — | — |
| 1-(cyclohexyloxy-carbonyloxy)ethyl 2-butyl-1-[[2'-(1H-tetrazol-5-yl)biphenyl-4-yl]-methyl]benzimidazole-7-carboxylate | — | — | 1.0 | — |
| pivaloyloxymethyl 2-butyl-1-[[2'-(1H-tetrazol-5-yl)biphenyl-4-yl]-methyl]-benzimidazole-7-carboxylate | — | — | — | 1.0 |
| Lactose | 93.0 | 93.0 | 93.0 | 93.0 |
| Corn starch | 20.0 | 20.0 | 20.0 | 20.0 |
| Polyethylene glycol 6000 | 6.0 | 6.0 | 6.0 | 6.0 |
| Hydroxypropyl cellulose | 4.0 | 4.0 | 4.0 | 4.0 |
| (Water) | (0.135 ml) | (0.135 ml) | (0.135 ml) | (0.135 ml) |
| Sub-total | 124.0 mg | 124.0 mg | 124.0 mg | 124.0 mg |
| Carboxylmethylcellulose calcium | 5.6 | 5.6 | 5.6 | 5.6 |
| Magnesium stearate | 0.4 | 0.4 | 0.4 | 0.4 |
| Total | 130.0 mg | 130.0 mg | 130.0 mg | 130.0 mg |

According to the present invention, orally administrable stable pharmaceutical compositions, in which decomposition of the active component is suppressed to maintain its high content ratio even after the lapse of time, can be provided, by having the active components, including the formula (V), incorporated with an oily substance whose melting point is relatively low.

The following references, which are refered to for their disclosure at various points in this application, are incorporated herein by reference.

EP-A-0425921
EP-A-0459136

What is claimed is:
1. A solid pharmaceutical composition for oral use, which comprises an effective amount of a compound of the formula

(I), in a crystalline form, having antagonistic action to angiotensin II

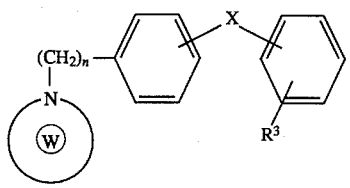

wherein the ring W is an optionally substituted N-containing heterocyclic residue; $R^3$ is a group capable of forming an anion or a group convertible thereinto; X is a direct bond or a spacer having an atomic length of two or less between the phenylene group and the phenyl group; and n is an integer of 1 or 2', and a polymer of alkylene oxide dispersed throughout the composition and is present in an amount from 0.005 to 0.15 weight per 1 weight of the composition.

2. A composition according to claim 1, wherein the compound of the formula (I) is a crystalline substance having a melting point of 100° to 200° C.

3. A composition according to claim 1, wherein the ring W in the compound of the formula (I) is a benzimidazole ring.

4. A composition according to claim 3, wherein the compound of the formula (I) is a benzimidazole-7 -carboxylic acid compound or a derivative thereof.

5. A composition according to claim 3, wherein the ring W in the compound of the formula (I) is a benzimidazole ring of the formula (III)

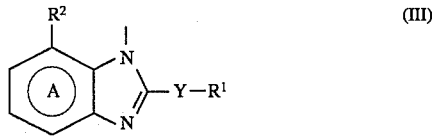

, wherein the ring A is a benzene ring; $R^1$ is hydrogen or an optionally substituted hydrocarbon residue; $R^2$ is an optionally esterified carboxyl group; Y is a bond, —O—, —S(O)m—, wherein m denotes 0, 1 or 2, or —N($R^4$)—, where $R^4$ is hydrogen or an optionally substituted alkyl group.

6. A composition according to claim 5, wherein $R^2$ in the benzimidazole ring of the formula (III) is a group represented by the formula —CO—D, wherein D is hydroxyl group or a lower ($C_{1-4}$) alkoxy whose alkyl portion is optionally substituted with hydroxyl, amino, halogen, a lower ($C_{2-6}$) alkanoyloxy, 1-lower ($C_{1-6}$) alkoxycarbonyloxy or a lower ($C_{1-4}$) alkoxy.

7. A composition according to claim 1, wherein $R^3$ in the compound of the formula (I) is an optionally substituted monocyclic heterocyclic residue.

8. A composition according to claim 7, wherein the heterocyclic residue is tetrazolyl.

9. A composition according to claim 1, the compound of the formula (I) is (±)-1 -(cyclohexyloxycarbonyloxy)ethyl 2-ethoxy-1-[[2'-(1H-tetrazol-5-yl )biphenyl-4-yl]methyl]-1H-benzimidazole-7-carboxylate.

10. A composition according to claim 1, the compound of the formula (I) is 2-butyl-1[[2'-(1H-tetrazol-5 -yl)biphenyl-4-yl]methyl]benzimidazole-7-carboxylic acid.

11. A composition according to claim 1, wherein the melting point of the polymer of alkylene oxide ranges from about 20° to 90° C.

12. A composition according to claim 1, wherein the amount of the polymer of alkylene oxide is less than 0.1 part by weight per 1 part of the composition by weight.

13. A composition according to claim 1, wherein the compound of the formula (I) is (±)-1-(cyclohexyloxycarbonyloxy)ethyl 2-ethoxy-1-[[2'-(1H-tetrazol-5-yl)biphenyl-4 -yl]methyl]-1H-benzimidazole-7-carboxylate.

14. A composition according to claim 1, wherein the alkylene oxide is ethylene oxide.

15. A composition according to claim 1, wherein the alkylene oxide has a molecular weight of greater than 1000.

16. A composition according to claim 1, wherein the composition is in a tablet form.

17. A solid pharmaceutical composition for oral use, comprising an effective amount of the compound (±)-1 -(cyclohexyloxycarbonyloxy) ethyl 2-ethoxy-1[[(2'-(1H-tetrazol-5 -yl)biphenyl-4-yl]methyl]-1H-benzimid-azole-7-carboxylate and polyethylene glycol (PEG) dispersed throughout the composition.

18. A composition according to claim 17, wherein the polyethylene glycol has a molecular weight of greater than 1000.

19. A composition according to claim 17, wherein the composition is in a tablet form.

20. A method for minimizing crystalline disorder of an active ingredient in a solid pharmaceutical composition for oral use, comprising:

(a) combining: (1) an active ingredient which is an effective amount of a compound of the formula (I), in a crystalline form, having antagonistic action to angiotensin II,

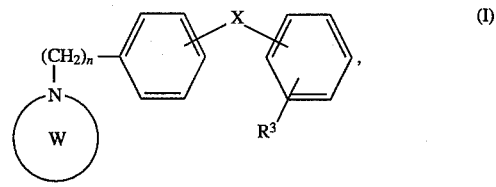

wherein the ring W is an optionally substituted N-containing heterocyclic residue; $R^3$ is a group capable of forming an anion or a group convertible thereinto; X is a direct bond or a spacer having an atomic length of two or less between the phenylene group and the phenyl group; and n is an integer of 1 or 2, and (2) a polymer of alkylene oxide present in an amount of from 0.005 to 0.15 weight per 1 weight of the composition; and (b) molding the combination of the active ingredient and the alkylene oxide into the solid pharmaceutical composition, whereby the crystalline disorder of the active ingredient (I) is minimized.

21. A method according to claim 20, wherein the molding step is tableting under elevated pressure to form a tablet of the composition.

22. A method according to claim 20, wherein the alkylene oxide is polyethylene glycol.

23. A method according to claim 20, wherein the active ingredient is

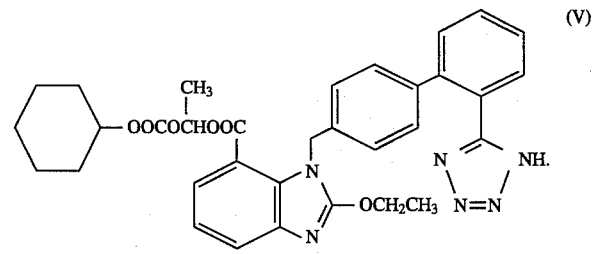

24. A composition according to claim 5, wherein the ring A contains, besides the group represented by $R^2$, further substituents selected from the group consisting of a halogen, a nitro, a cyano, a $(C_{1-4})$ alkyl, a $(C_{1-4})$ alkoxy, an amino, an N—$(C_{1-4})$ alkylamino, an N,N-di-$(C_{1-4})$ alkylamino, an N-arylamino, an alicyclic amino, tetrazolyl, trifluoromethanesulfonic acid amide, phosphoric acid, sulfonic acid, and a group represented by the formula —CO—D'—, wherein D' is selected from the group consisting of a hydroxyl and a $(C_{1-4})$ alkoxy.

25. A composition according to claim 24, wherein said tetrazolyl, trifluoromethanesulfonic acid amide, phosphoric acid, and sulfonic acid are protected with a group selected from $(C_{1-4})$ alkyl, $C_{2-5}$ alkanoyl, and optionally substituted benzoyl.

26. A composition according to claim 24, wherein one or two of said further substituents are substituted simultaneously on optional positions of ring A.

27. A composition according to claim 24, wherein D' is a $(C_{1-4})$ alkoxy whose alkyl portion is substituted with a group selected from a hydroxyl, a $(C_{1-4})$ alkoxy, a $(C_{2-6})$ alkanoyloxy, and a $(C_{1-6})$ alkoxycarbonyloxy.

* * * * *

UNITED STATES PATENT AND TRADEMARK OFFICE
CERTIFICATE OF CORRECTION

PATENT NO.      : 5,534,534
APPLICATION NO. : 07/978290
DATED           : July 9, 1996
INVENTOR(S)     : Tadashi Makino, Yoshio Mizukami and Jun-ichi Kikuta It is certified that error appears in the above-identified patent and that said Letters Patent is hereby corrected as shown below:

On the cover page, item [75], the second inventor's name "Yashio Mizukami" should be --Yoshio Mizukami--.

Col. 21, claim 1, the formula on lines 3-11 should be:

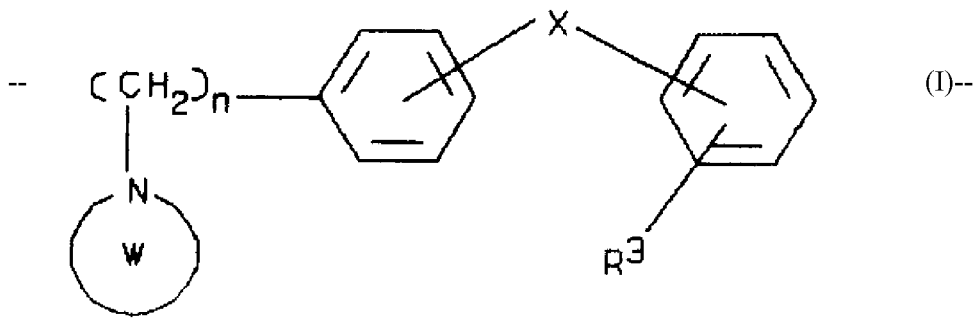

Col. 21, claim 1, line 17, "1 or 2' " should be --1 or 2--.

Col. 21, claim 6, line 49, "($C_{14}$)" should be --($C_{1-4}$)--.

Col. 21, claim 9, line 55, "claim 1, the" should be --claim 1, wherein the--.

Col. 21, claim 10, line 59, "claim 1, the" should be --claim 1, wherein the--.

Col. 21, claim 10, line 60, "2-butyl-1[[" should be --2-butyl-1-[[--.

Col. 21, claim 10, line 60, "5- yl)" should be --5-yl)--.

Col. 22, claim 13, line 1, "claim 1" should be --claim 11--.

Col. 22, claim 17, line 13, "2-ethoxy-1[[" should be --2-ethoxy-1-[[--.

Col. 22, claim 17, line 14, "razol-5 -yl)" should be --razol-5-yl)--; "benzimid-azole" should be --benzimidazole--.

UNITED STATES PATENT AND TRADEMARK OFFICE
CERTIFICATE OF CORRECTION

PATENT NO. : 5,534,534
APPLICATION NO. : 07/978290
DATED : July 9, 1996
INVENTOR(S) : Tadashi Makino, Yoshio Mizukami and Jun-ichi Kikuta It is certified that error appears in the above-identified patent and that said Letters Patent is hereby corrected as shown below:

Col. 23, claim 24, line 6, "—CO—D'—" should be -- —CO—D' --.

Signed and Sealed this

Twenty-sixth Day of February, 2008

JON W. DUDAS
*Director of the United States Patent and Trademark Office*